(12) United States Patent
Chang et al.

(10) Patent No.: US 11,913,876 B2
(45) Date of Patent: Feb. 27, 2024

(54) OPTICAL WATER-QUALITY DETECTION APPARATUS

(71) Applicant: INDUSTRIAL TECHNOLOGY RESEARCH INSTITUTE, Hsinchu (TW)

(72) Inventors: Chia-Jung Chang, Douliu (TW); Jui-Hung Tsai, Toufen (TW); Ying-Hao Wang, Neipu Township (TW); Chih-Hao Hsu, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 17/885,073

(22) Filed: Aug. 10, 2022

(65) Prior Publication Data
US 2023/0152219 A1    May 18, 2023

(30) Foreign Application Priority Data
Nov. 17, 2021    (TW) .................................. 110142782

(51) Int. Cl.
*G01N 21/33* (2006.01)
*G02B 27/14* (2006.01)
(Continued)

(52) U.S. Cl.
CPC .............. *G01N 21/33* (2013.01); *G01N 21/31* (2013.01); *G01N 21/3577* (2013.01);
(Continued)

(58) Field of Classification Search
CPC ................... G01N 21/33; G01N 33/18; G01N 2201/0636; G01N 21/94; G01N 21/3577;
(Continued)

(56) References Cited

U.S. PATENT DOCUMENTS 10,139,386 B2    11/2018    Smeeton et al.
11,519,861 B2 *  12/2022    Prater .................. G01N 21/359
(Continued)

FOREIGN PATENT DOCUMENTS

CN    103261886 A    8/2013
CN    203534961 U    4/2014
(Continued)

OTHER PUBLICATIONS

Taiwanese Office Action and Search Report for Taiwanese Application No. 110142782 dated Oct. 4, 2022.
(Continued)

*Primary Examiner* — Jennifer D Bennett
*Assistant Examiner* — Erin R Garber
(74) *Attorney, Agent, or Firm* — Birch, Stewart, Kolasch & Birch, LLP

(57) ABSTRACT

An optical water-quality detection apparatus includes a detection device, a biofilm-inhibition light source, a detection light source and a sensor. The detection device includes a detection chamber. The biofilm-inhibition light source is disposed outside the detection chamber and configured to emit biofilm-inhibition light. The detection light source is disposed outside the detection chamber and configured to emit detection light. The sensor is configured to sense the detection light penetrating the detection chamber. A beam of the detection light and a beam of the inhibition light overlaps as penetrating the detection chamber.

16 Claims, 9 Drawing Sheets

(51) Int. Cl.
*G01N 33/18* (2006.01)
*G01N 21/3577* (2014.01)
*G01N 21/31* (2006.01)
*G02B 5/20* (2006.01)
*G01N 21/77* (2006.01)
*G01N 21/01* (2006.01)

(52) U.S. Cl.
CPC ........... *G01N 33/18* (2013.01); *G02B 27/141* (2013.01); *G01N 21/01* (2013.01); *G01N 2021/7763* (2013.01); *G01N 2201/0636* (2013.01); *G02B 5/20* (2013.01)

(58) Field of Classification Search
CPC ................ G01N 21/359; G01N 21/78; G01N 2021/7763; G01N 21/31; G01N 33/1826; G02B 27/141; G02B 5/20; A61L 2/10; Y02A 20/20
See application file for complete search history.

(56) References Cited

U.S. PATENT DOCUMENTS

| | | |
|---|---|---|
| 2011/0273757 A1 | 11/2011 | Kobayashi |
| 2016/0213444 A1* | 7/2016 | Kiremitci ............. A61C 1/0076 |
| 2018/0059015 A1* | 3/2018 | Li ........................ G01N 33/146 |
| 2018/0143173 A1* | 5/2018 | Chang .................... A23N 12/02 |
| 2019/0233309 A1 | 8/2019 | Lu et al. |
| 2020/0011787 A1* | 1/2020 | Dalby ................ G01N 33/2823 |

FOREIGN PATENT DOCUMENTS

| | | |
|---|---|---|
| CN | 102798602 B | 6/2015 |
| CN | 212083246 U | 12/2020 |
| CN | 113615606 A | 11/2021 |
| JP | 2021-32572 A | 3/2021 |
| TW | I384217 B | 2/2013 |
| TW | I477760 B | 3/2015 |
| TW | M583543 U | 9/2019 |
| TW | 202043733 A | 12/2020 |

OTHER PUBLICATIONS

Bilotta et al., "Understanding the influence of suspended solids on water quality and aquatic biota," Water Research, vol. 42, Mar. 29, 2008, pp. 2849-2861.

Liu et al., "A Review on Optical Measurement Method of Chemical Oxygen Demand in Water Bodies," IFIP International Federation for Information Processing, Springer International Publishing AG, 2016, pp. 619-636.

Shenashen et al., "Architecture of optical sensor for recognition of multiple toxic metal ions from water," Journal of Hazardous Materials, vol. 260, Jun. 10, 2013, pp. 833-843.

* cited by examiner

OPTICAL WATER-QUALITY DETECTION APPARATUS

This application claims the benefit of Taiwan application Serial No. 110142782, filed Nov. 17, 2021, the subject matter of which is incorporated herein by reference.

TECHNICAL FIELD

The disclosure relates in general to an optical water-quality detection apparatus.

BACKGROUND

In response to needs for water quality testing, building water quality detection apparatus is necessary. In the storage tank for water quality detection, microorganism attachment or growth is often formed on a tank wall to produce biofilm which causes obvious interference to the water quality detection. Therefore, frequent cleaning is required to maintain the accuracy and stability of the detection results. However, the maintenance costs and manpower burden on the operator.

SUMMARY

According to an embodiment, an optical water-quality detection apparatus is provided. The optical water-quality detection apparatus includes a detection chamber device, a biofilm-inhibited light source, a detection light source and a first sensor. The detection chamber device includes a detection chamber. The biofilm-inhibited light source is disposed outside the detection chamber and configured to emit an inhibition light. The detection light source is disposed outside the detection chamber and configured to emit a detection light. The first sensor is configured to sense the detection light penetrating the detection chamber. Wherein a beam of the detection light and a beam of the inhibition light overlap each other when penetrating the detection chamber.

The above and other aspects of the disclosure will become better understood with regard to the following detailed description of the preferred but non-limiting embodiment(s). The following description is made with reference to the accompanying drawings.

Figure 1:
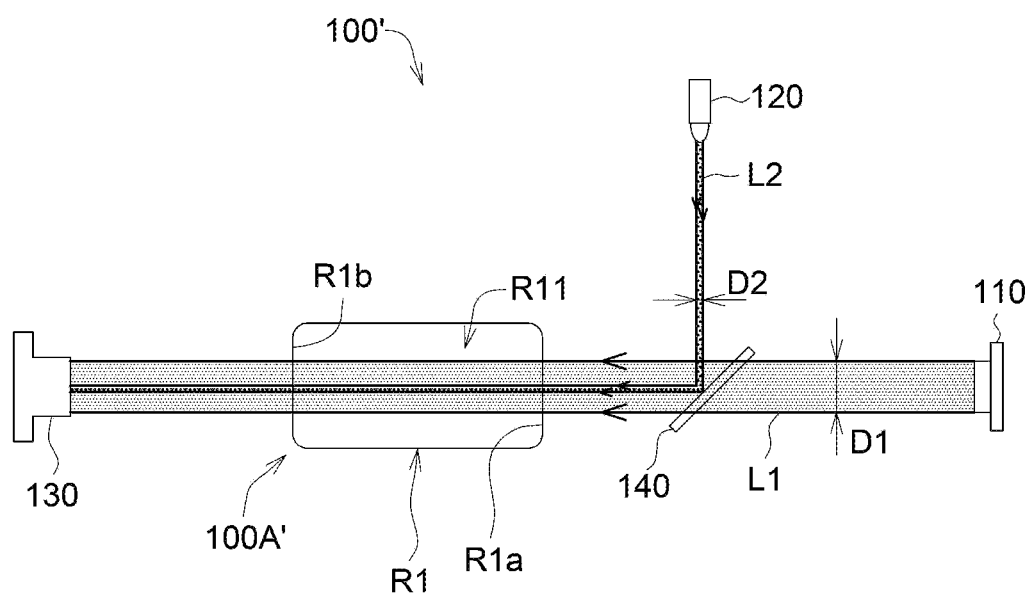
FIG. 1 shows a schematic diagram of an optical path of the optical water-quality detection apparatus according to an embodiment of the disclosure.

In the following detailed description, for purposes of explanation, numerous specific details are set forth in order to provide a thorough understanding of the disclosed embodiments. It will be apparent, however, that one or more embodiments could be practiced without these specific details. In other instances, well-known structures and devices are schematically shown in order to simplify the drawing.

DETAILED DESCRIPTION

Referring to FIG. 1, FIG. 1 shows a schematic diagram of an optical path of the optical water-quality detection apparatus 100' according to an embodiment of the disclosure. The optical water-quality detection apparatus 100' includes a detection chamber device 100A, a biofilm-inhibited light source 110, a detection light source 120, a first sensor 130 and a first light-splitting mirror 140. The detection chamber device 100A includes a detection chamber R1. The biofilm-inhibited light source 110 is disposed outside the detection chamber R1 and configured to emit inhibition light L1. The detection light source 120 is disposed outside the detection chamber R1 and configured to emit detection light L2. The first sensor 130 is configured to sense the detection light L2 after the detection light L2 penetrates the detection chamber R1. The beam of the detection light L2 and the beam of the inhibition light L1 overlap each other when they travel within the detection chamber R1. For example, the beam of the detection light L2 has a spot area (a cross-sectional area of a beam diameter D2) is less than or equal to another spot area (a cross-sectional area of a beam diameter D1) of the beam of the inhibition light L1, and the spot area of the detection light L2 completely overlap the spot area of the inhibition light L1. As a result, while a to-be-tested liquid (not shown) in the detection chamber R1 is under detection, the inhibition light L1 could inhibit the activity of the biofilm, and accordingly it could avoid the detection accuracy effected by biofilm and maintain a proper detection accuracy longer.

As shown in FIG. 1, the detection chamber R1 is hollow, for example. The detection chamber device 100A has a liquid storage space R11 disposed within the detection chamber R1, and the liquid storage space R11 could receive the to-be-tested liquid. The detection light L2 penetrates the detection chamber R1 through the to-be-tested liquid. The to-be-tested liquid is, for example, drinking water, factory wastewater, stream water, agricultural channel water, rainwater or other liquids that require to be tested. The detection chamber R1 includes a light-incident side R1a and a light-exit side R1b, and the inhibition light L1 and the detection light L2 is incident into the liquid storage space R11 through the light-incident side R1a and leave the liquid storage space R11 through the light-exit side R1b. The inhibition light L1 and the detection light L2 penetrate the liquid storage space R11 could inhibit the activity of the biofilm, slow down growth rate of the biofilm on a surface, prolong operation life cycle of the optical water-quality detection apparatus 100' and/or increase or stabilize the detection accuracy. In addition, since the beam of the detection light L2 overlaps the beam of the inhibition light L1, the biofilm could be inhibited by the inhibition light L1 within the range of the beam diameter of the detection light L2.

Figure 2A:
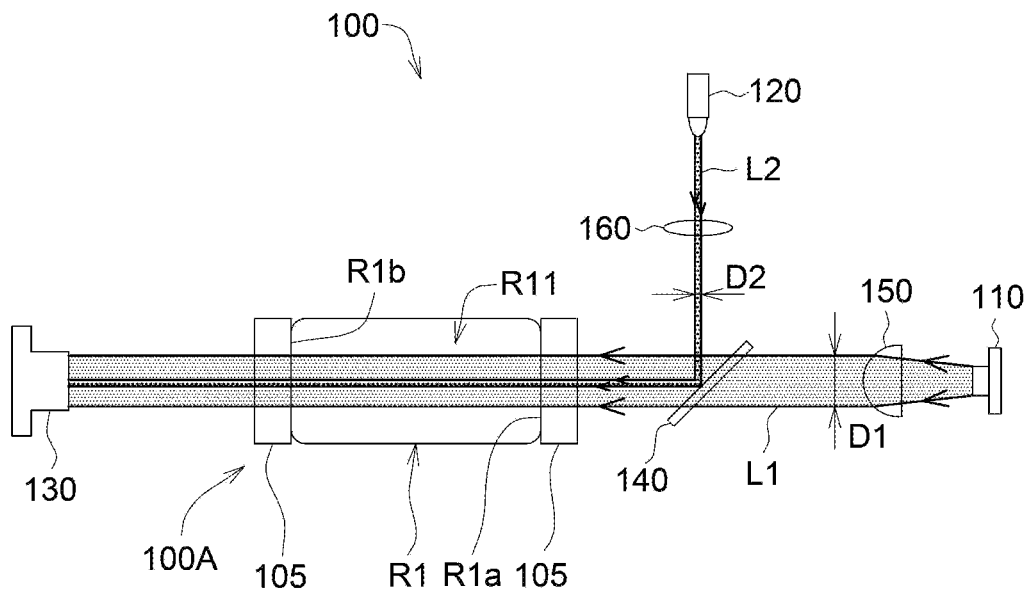
FIG. 2A shows a schematic diagram of the optical path of the optical water-quality detection apparatus according to another embodiment of the disclosure.
Figure 2B:
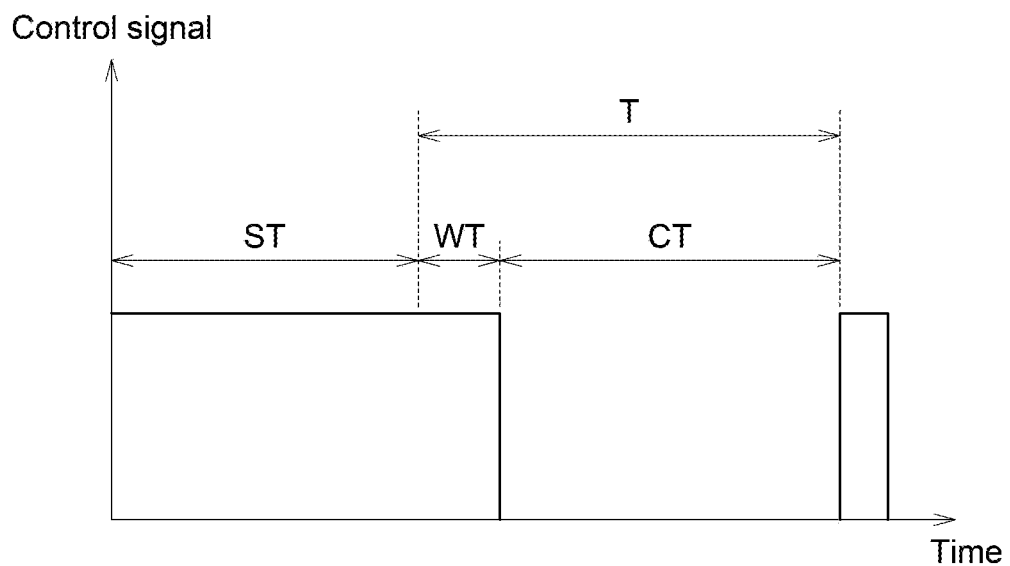
FIG. 2B shows a diagram of a working mode of the optical water-quality detection apparatus of FIG. 2A.

Referring to FIGS. 2A to 2B. FIG. 2A shows a schematic diagram of the optical path of the optical water-quality detection apparatus 100 according to another embodiment of the disclosure, and FIG. 2B shows a diagram of a working mode of the optical water-quality detection apparatus 100 of FIG. 2A.

The optical water-quality detection apparatus 100 includes the detection chamber device 100A, two detection windows 105, the biofilm-inhibited light source 110, the detection light source 120, the first sensor 130, the first light-splitting mirror 140, a first condensing lens 150 and a second condensing lens 160.

The detection chamber device 100A includes the detection chamber R1. The biofilm-inhibited light source 110 is disposed outside the detection chamber R1 and configured to emit inhibition light L1. The detection light source 120 is disposed outside the detection chamber R1 and configured to emit detection light L2. The first sensor 130 is configured to sense the detection light L2 after the detection light L2 penetrates the liquid storage space R11. The beam of the detection light L2 and the beam of the inhibition light L1 overlap each other during penetrating the liquid storage space R11. For example, the spot area (the cross-sectional area of the beam diameter D2) of the beam of the detection light L2 is less than or equal to the spot area (the cross-sectional area of the beam diameter D1) of the beam of the inhibition light L1, and the spot area of the detection light L2 is completely (or entirely) overlapped with the spot area of the inhibition light L1.

The detection light L2 penetrates the liquid storage space R11 through the to-be-tested liquid. The to-be-tested liquid in the liquid storage space R11 contacts the detection window 105, and the biofilm is formed on the surface of the detection window 105. The biofilm is structured community formed by Exopoly Saccharides (EPS) generated by the microbial cell itself surrounding the microbial cell and the attaching to an inert or biofilm surface immersed in liquid. The biofilms could include many different kinds of microorganisms, such as bacteria, archaea, protozoa, fungi, algae, etc.

The detection chamber R1 includes the light-incident side R1a and the light-exit side R1b, and the inhibition light L1 and the detection light L2 enter the liquid storage space R11 through the light-incident side R1a and leave the liquid storage space R11 through the light-exit side R1b. The detection window 105 is, for example, glass, such as quartz glass. The two detection windows 105 are light-transmissive and respectively disposed on two opposite sides of the detection chamber R1, for example, the light-incident side R1a and the light-exit side R1b. The inhibition light L1 and the detection light L2 penetrate the liquid storage space R11 through the detection windows 105 for inhibiting the activity of the biofilm on the detection window 105, slowing down the growth of the biofilm on the surface of the detection window 105 and prolonging the operation life cycle of the optical water-quality detection apparatus 100 and/or increasing or stabilize detection accuracy. In addition, since the beam of the detection light L2 overlaps the beam of the inhibition light L1, the biofilm on the detection window 105 could be inhibited by the inhibition light L1 within the range of the beam diameter of the detection light L2.

In an embodiment, the biofilm-inhibited light source 110 is, for example, an ultraviolet light source, the inhibition light L1 has a center wavelength, for example, 275 nanometers (nm), the detection light source 120 is, for example, a halogen light source having a wide wavelength range, and the detection light L2 is, for example, visible light-near infrared light (VIS-NIR). The first sensor 130 could react to the detection light L2 and generate signal, but does not react to the inhibition light L1. For example, a filter (not shown in FIG. 2A) could be disposed in front of the first sensor 130 to filter out the signal of the inhibition light L1. Alternatively, the corresponding photo sensor could be selected according to the wavelength range of the detection light L2. For example, for the UV spectrum, gallium nitride photodiodes could be selected, and/or, for visible light to near-infrared light, silicon photodiodes could be selected. As a result, the optical water-quality detection apparatus 100 could detect a specific composition of the to-be-tested liquid in the liquid storage space R11 by the detection light L2.

In an embodiment, the first sensor 130 is, for example, a silicon photodiode (Si PD), and the first light-splitting mirror 140 could reflect light having a center wavelength of 850 nm, so the detection light L2 incident into the first sensor 130 has the center wavelength of 850 nm. The first sensor 130 could react to the detection light L2 having the center wavelength of 850 nm and generate signal so as to detect Suspended Solids (SS) of the to-be-tested liquid in the liquid storage space R11, and such test is called "SS detection". In another embodiment, the first sensor 130 could react to light having the center wavelength of 546 nm, 650 nm or combination thereof and generate signal, or the first sensor 130 could react to light be partially absorbed or scattered by suspended solids in the to-be-tested liquid for performing SS detection. In another embodiment, the first light-splitting mirror 140 could reflect light having the center wavelength of 450 nm, and thus the detection light L2 incident into the first sensor 130 has the center wavelength of 450 nm. The first sensor 130 could react to the detection light L2 having the center wavelength of 450 nm and generate signal so as to detect concentration of copper ion of the to-be-tested liquid in the liquid storage space R11, and such detection is called "copper ion concentration detection".

As shown in FIG. 2A, in terms of relative positional relationship, the biofilm-inhibited light source 110, the detection light source 120, the first light-splitting mirror 140, the first condensing lens 150 and the second condensing lens 160 are disposed on a side of the detection chamber R1, such as the light-incident side R1a, and the first sensor 130 is disposed on the opposite side of the detection chamber R1, such as the light-exit side R1b.

As shown in FIG. 2A, the first light-splitting mirror 140 is disposed between the biofilm-inhibited light source 110 and the detection chamber R1, or disposed between the detection light source 120 and the detection chamber R1, and is configured to guide the inhibition light L1 and the detection light L2 enter the liquid storage space R11. The first light-splitting mirror 140 is, for example, a dichroic beam splitter, wherein the first light-splitting mirror 140 allows the inhibition light L1 to travel through but reflects the detection light L2. As a result, the inhibition light L1 and the detection light L2 together (or at the same time) could be incident into the first sensor 130 from the first light-splitting mirror 140 after being traveling to the first light-splitting mirror 140 in different directions.

As shown in FIG. 2A, the first condensing lens 150 and the biofilm-inhibited light source 110 are disposed opposite to each other. The first condensing lens 150 is configured to adjust the beam diameter D1 of the inhibition light L1. The second condensing lens 160 and the detection light source 120 are opposite to each other. The second condensing lens 160 is configured to adjust the beam diameter D2 of the detection light L2. As a result, due to the design of the first condensing lens 150 and the second condensing lens 160, the beam of the detection light L2 could overlap the beam of the inhibition light L1. In an embodiment, the first condensing lens 150 is, for example, a single lens or a lens group formed by gluing several lenses to each other. The aforementioned lens could include a plano-convex lens, a convex plano lens or other type of light-transmissive lens that could change the beam diameter D1 of the inhibition light L1. The second condensing lens 160 has the structure similar to or the same as that of the first condensing lens 150, and the similarities will not be repeated here. As long as the beam diameter D2 of the detection light L2 could change, the embodiment of the disclosure does not limit the structure of the second condensing lens 160.

In addition, in the embodiment, the first condensing lens 150 and the biofilm-inhibited light source 110 could be disposed separately (that is, without physical connection). Alternatively, the first condensing lens 150 and the biofilm-inhibited light source 110 are directly connected. Similarly, the second condensing lens 160 and the detection light source 120 could disposed separately (that is, without physical connection). Alternatively, the second condensing lens 160 and the detection light source 120 are directly connected.

As shown in FIG. 2B, ST represents the warm-up time of the light source, WT represents the illuminating time (ON) of the light source, CT represents the non-illuminating time (OFF) of the light source, and T represents a work period. The warm-up time could speed up the light source to enter the stable period, provide stability in the work execution, and reduce the required working time. The light source does not emit light during the non-illuminating time CT, and the light source is cooled. In the embodiment, the illuminating time WT immediately follows the warm-up time ST. However, in another embodiment, the illuminating time WT and the warm-up time ST could be separated from each other, that is, a non-illuminating time is inserted between the warm-up time ST and the illuminating time WT. Although not shown, the working modes of the biofilm-inhibited light source 110 and the detection light source 120 could be controlled by a processor (not shown), and such processor could be electrically connected to the light source and/or sensor herein to control the operation of these components, and receive and/or analyze the signal from the sensor.

The working sequence of the biofilm-inhibited light source 110 and the detection light source 120 could be the same or different. For example, for the biofilm-inhibited light source 110, WT:CT:ST=1:4:10. In a preferred embodiment, WT:CT:ST=10 millisecond (ms):40 ms:100 ms. For the detection light source 120 (for example, halogen lamp), WT:CT:ST=1:3:4. In a preferred embodiment, WT:CT:ST=250 ms:750 ms:1000 ms, but the embodiments of the disclosure are not limited thereto.

The working frequencies of the biofilm-inhibited light source 110 and the detection light source 120 could be the same or different. For example, for the biofilm-inhibited light source 110, 80 work period T could be executed every 20 minutes; however, such exemplification is not meant to be for limiting. For the detection light source 120 (for example, halogen lamp), 5 work period T could be executed every 20 minutes; however, such exemplification is not meant to be for limiting. In the embodiment, one illuminating time WT and one non-illuminating time CT are defined as one work period T. Although not shown, the aforementioned illuminating time WT, the non-illuminating time CT and/or warm-up time ST could also be controlled by the processor.

In addition, the working mode of the optical water-quality detection apparatus in other embodiments of the disclosure is the same as that shown in FIG. 2A, and the similarities will not be repeated here.

Figure 3:
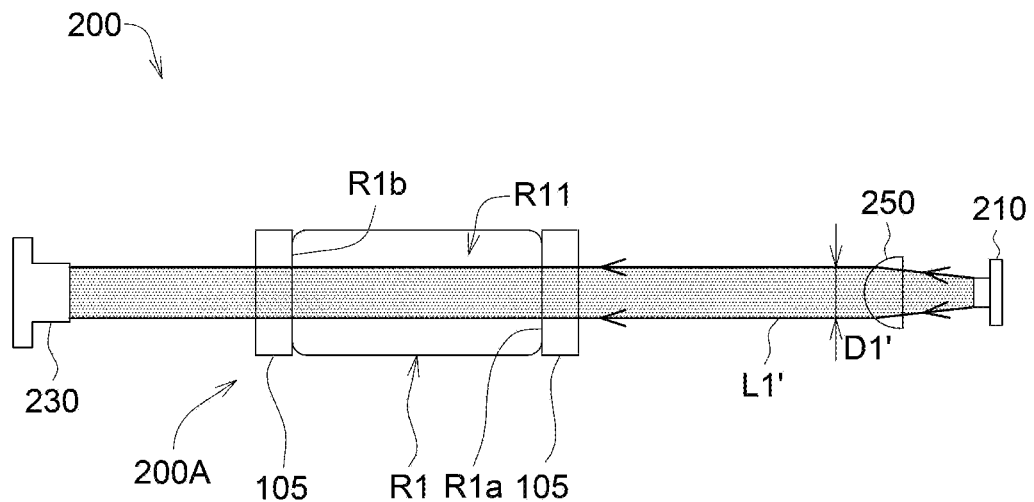
FIG. 3 shows a schematic diagram of the optical path of an optical water-quality detection apparatus according to another embodiment of the disclosure.

Referring to FIG. 3, FIG. 3 shows a schematic diagram of the optical path of an optical water-quality detection apparatus 200 according to another embodiment of the disclosure. The optical water-quality detection apparatus 200 includes a detection chamber device 200A, two detection windows 105, a biofilm-inhibited light source 210, a sensor 230 and a first condensing lens 250. The optical water-quality detection apparatus 200 has the technical features similar to or the same as that of the optical water-quality detection apparatus 100 expect that the optical water-quality detection apparatus 200 could omit the detection light source 120, the first light-splitting mirror 140 and the second condensing lens 160.

In the embodiment, the biofilm-inhibited light source 210 is configured to emit an inhibition light L1' which also has the detection function of the aforementioned detection light L2. In an embodiment, the biofilm-inhibited light source 210 is, for example, an ultraviolet light source, the inhibition light L1' has the center wavelength of, for example, 275 nm. The sensor 230 is, for example, a gallium nitride (GaN) sensor which could react to the inhibition light L1' after the inhibition light L1' penetrates the liquid storage space R11, and generate signal so as to detect the chemical oxygen demand (COD) of the to-be-tested liquid in the liquid storage space R11. Such detection optical path is called the "COD detection optical path". The biofilm-inhibited light source 210 has a center wavelength which is selected from 250 nm, 254 nm or combination thereof or other spectrum which could be absorbed by organic matters in the to-be-tested liquid for performing COD detection. Although not shown, the detection result could be transmitted to an external electronic device through a wireless communication module, and such electronic device could display a trend of the detection result over a period of time (water-quality monitoring).

As shown in FIG. 3, the first condensing lens 250 and the biofilm-inhibited light source 210 are disposed opposite to each other. The first condensing lens 250 is configured to adjust the beam diameter D1' of the inhibition light L1'. In an embodiment, the first condensing lens 250 and the biofilm-inhibited light source 210 could be configured separately (that is, without physical connection). Alternatively, the first condensing lens 250 and the biofilm-inhibited light source 210 are directly connected.

As shown in FIG. 3, in terms of relative positional relationship, the biofilm-inhibited light source 210 and the first condensing lens 250 could be disposed on a side of the detection chamber R1, such as the light-incident side R1a, and the sensor 230 could be disposed on the opposite side of the detection chamber R1, such as the light-exit side R1b.

Figure 4:
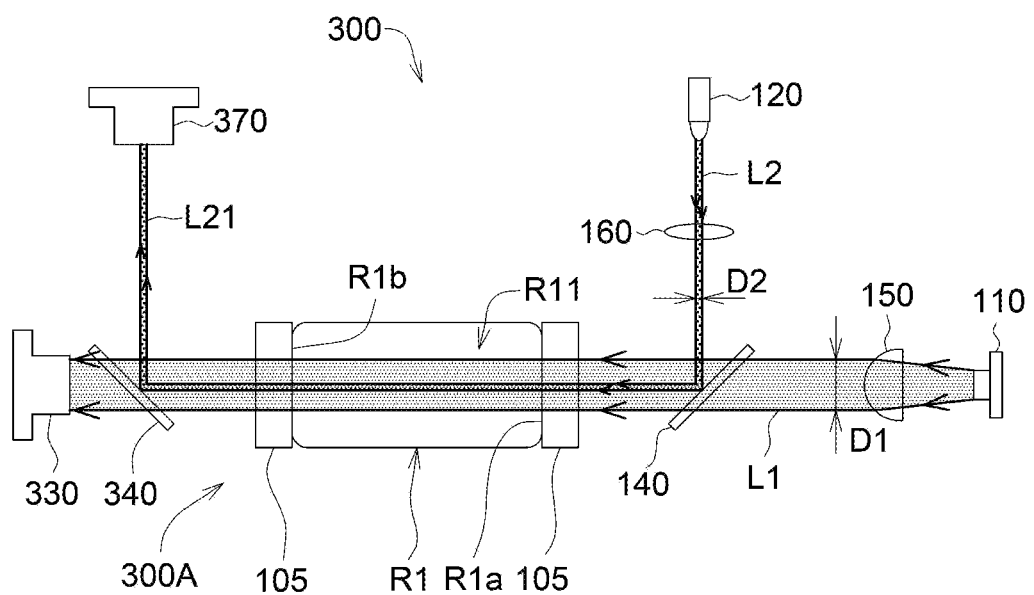
FIG. 4 shows a schematic diagram of the optical path of an optical water-quality detection apparatus according to another embodiment of the disclosure.

Referring to FIG. 4, FIG. 4 shows a schematic diagram of the optical path of an optical water-quality detection apparatus 300 according to another embodiment of the disclosure. The optical water-quality detection apparatus 300 includes a detection chamber device 300A, two detection windows 105, the biofilm-inhibited light source 110, the detection light source 120, the first sensor 330, the first light-splitting mirror 140, the first condensing lens 150, the second condensing lens 160, a second light-splitting mirror 340 and a second sensor 370. The optical water-quality detection apparatus 300 has technical features similar to or the same as that of the optical water-quality detection apparatus 100 expect that the optical water-quality detection apparatus 300 further includes the second light-splitting mirror 340 and the second sensor 370.

As shown in FIG. 4, the first sensor 330 is, for example, a GaN detector which could react to the inhibition light L1 after the inhibition light L1 penetrates the detection chamber R1 and generate signal so as to sense the chemical oxygen demand of the to-be-tested liquid in the liquid storage space R11.

In the embodiment, the same beam of the detection light L2 could detect a variety of different properties of the to-be-tested liquid in the liquid storage space R11, and it will be further described below.

As shown in FIG. 4, the second sensor 370 is located outside the detection chamber R1. The second light-splitting mirror 340 is located outside the detection chamber R1 and adjacent to the light-exit side R1b to guide the detection light L2 to the second sensor 370. The second light-splitting mirror 340 is, for example, a dichroic beam splitter which allows the inhibition light L1 to travel through but reflects the detection light L2, for example, the first waveband light L21 of the reflection detection light L2. The second sensor 370 is configured to generate signal by reacting to the first waveband light L21 so as to detect a specific composition of the to-be-tested liquid in the liquid storage space R11. In an embodiment, the second sensor 370 is, for example, a silicon photodiode, and the second light-splitting mirror 340 could reflect light with a center wavelength of 850 nm, so the first waveband light L21 incident into the second sensor 370 includes the center wavelength of 850 nm. The second sensor 370 could react to the first waveband light L21 and generates signal so as to detect suspended solids within the to-be-tested liquid in the liquid storage space R11 (SS detection). In another embodiment, the second light-splitting mirror 340 could reflect light with a center wavelength of 450 nm, so the first waveband light L21 incident into the second sensor 370 includes the center wavelength of 450 nm. The second sensor 370 could react to the first waveband light L21 and generates signal so as to detect the concentration of copper ions of the to-be-tested liquid in the liquid storage space R11.

As shown in FIG. 4, in terms of relative positional relationship, the biofilm-inhibited light source 110, the detection light source 120, the first light-splitting mirror 140, the first condensing lens 150 and the second condensing lens 160 could be disposed on a side of the detection chamber R1, such as the light-incident side R1a, and the first sensor 330, the second light-splitting mirror 340 and the second sensor 370 could be disposed on the opposite side of the detection chamber R1, such as the light-exit side R1b.

Figure 5:
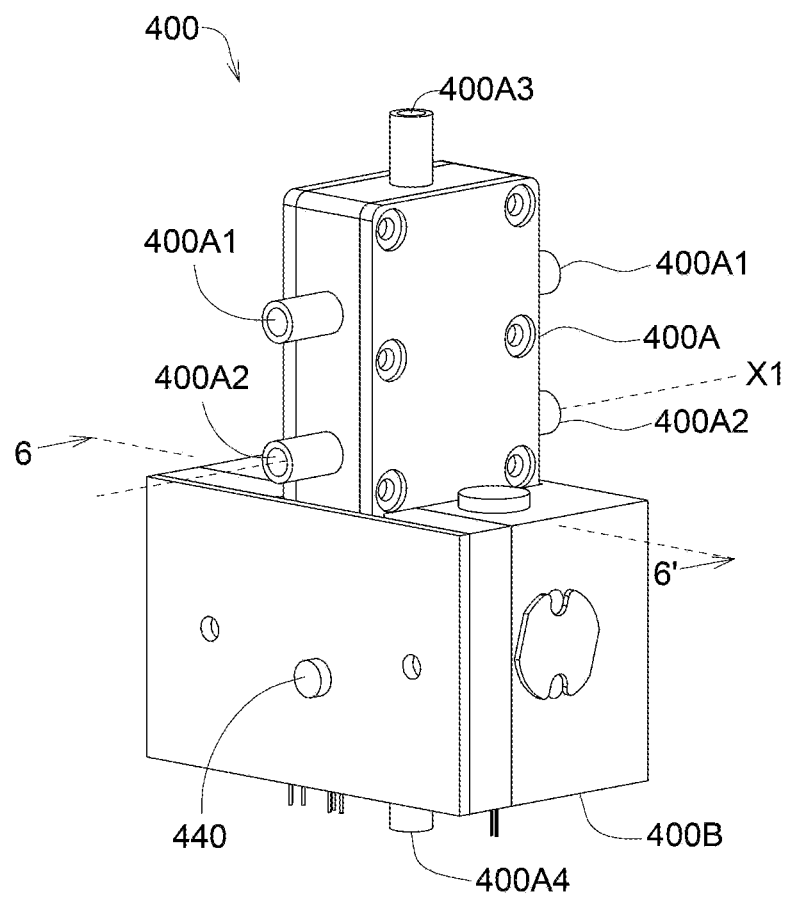
FIG. 5 shows a schematic diagram of an optical water-quality detection apparatus according to another embodiment of the disclosure.
Figure 6:
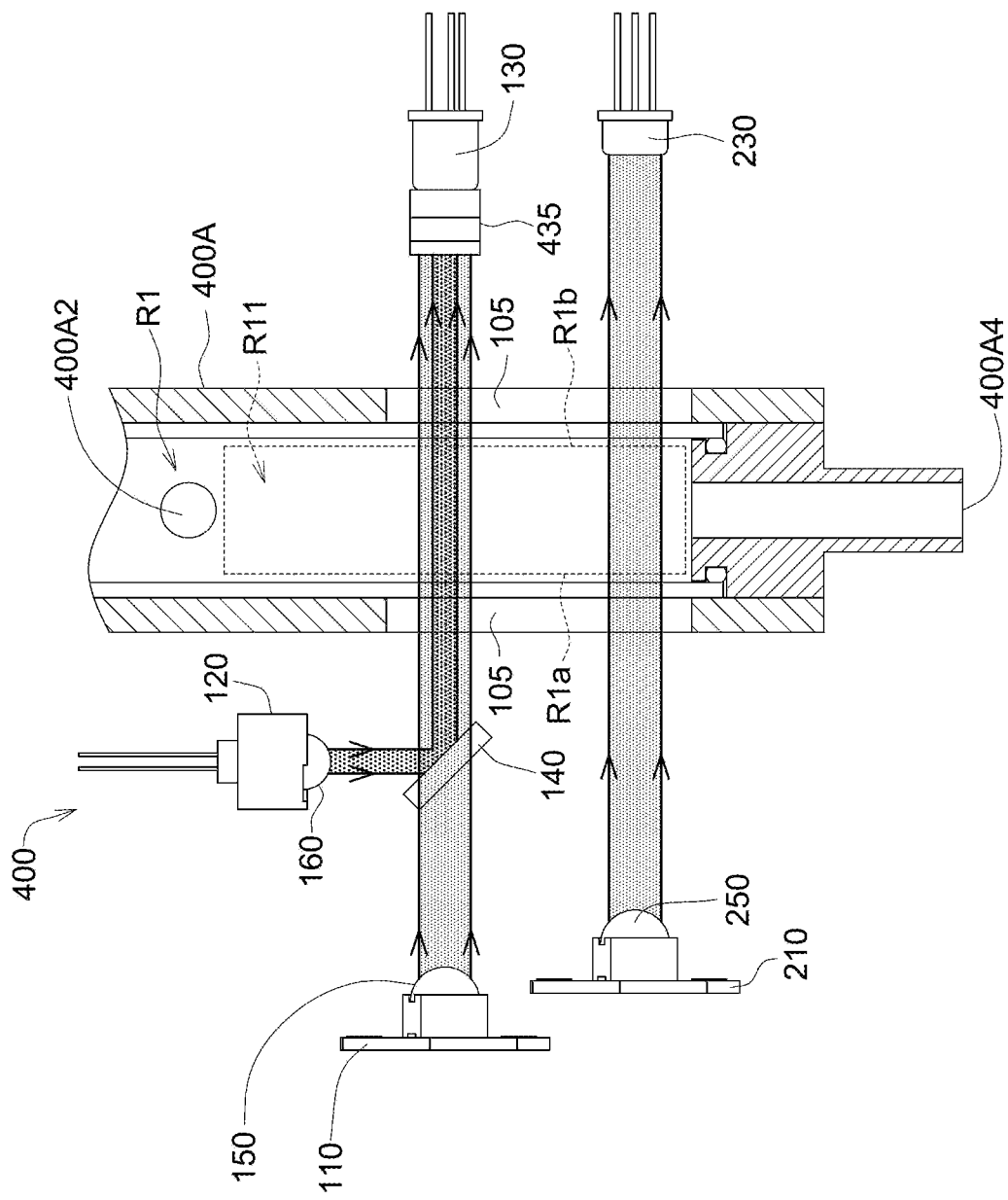
FIG. 6 shows a schematic diagram of a cross-sectional view of the optical water-quality detection apparatus of FIG. 5 along the direction 6-6'.

Referring to FIGS. 5 to 6. FIG. 5 shows a schematic diagram of an optical water-quality detection apparatus 400 according to another embodiment of the disclosure, and FIG. 6 shows a schematic diagram of a cross-sectional view of the optical water-quality detection apparatus 400 of FIG. 5 along the direction 6-6'. The optical water-quality detection apparatus 400 includes a detection chamber device 400A, a sensing base 400B, a detection chamber device 400A, two detection windows 105, the biofilm-inhibited light source 110, the detection light source 120, the first sensor 130, and the first light-splitting mirror 140, the first condensing lens 150, the second condensing lens 160, the biofilm-inhibited light source 210, the first condensing lens 250, the sensor 230, a first filter 435 and a holder 440.

As shown in FIGS. 5 and 6, the detection chamber device 400A includes a liquid storage space R11 within the detection chamber R1, two detection windows 105, a liquid inlet 400A1, an overflow outlet 400A2, a reagent inlet 400A3, and the liquid outlet 400A4. The two detection windows 105 are disposed on two opposite sides of the detection chamber R1. The liquid inlet 400A1, the overflow outlet 400A2, the reagent inlet 400A3 and the liquid outlet 400A4 are communicated with the liquid storage space R11. The liquid inlet 400A1 is disposed within the detection chamber R1 and communicated with the liquid storage space R11, and the to-be-tested liquid could enter the liquid storage space R11 from the liquid inlet 400A1. A reagent (not shown) could enter the liquid storage space R11 from the reagent inlet 400A3 to be mixed with the to-be-tested liquid. For example, when performing copper ion concentration detection, the copper ion reagent could flow into the liquid storage space R11 from the reagent inlet 400A3 to be mixed with the to-be-tested liquid. When the to-be-tested liquid contains copper ions of different concentrations, the mixed solution will show a color change in chromaticity. The overflow outlet 400A2 communicates with the liquid storage space R11 and has a central axis X1. The central axis X1 of the overflow outlet 400A2 is located between the detection windows 105 and the reagent inlet 400A3 for allowing the redundant to-be-tested liquid to be discharged. As a result, the to-be-tested liquid in the liquid storage space R11 could be maintained at a fixed volume (constant). In addition, when the quantitative copper ion reagent flows into the liquid storage space R11, the mixture of the to-be-tested liquid and the copper ion reagent could have a fixed ratio composition for ensuring the accuracy of the copper ion concentration detection. In addition, the liquid outlet 400A4 is located at a bottom surface or a bottom portion of the detection chamber device 400A, and the to-be-tested liquid in the liquid storage space R11 could be discharged out of the detection chamber R1 through the liquid outlet 400A4. When the to-be-tested liquid is under detection, the drainage port 400A4 could be closed or plugged for preventing the to-be-tested liquid from being discharged.

At least one optical element of the aforementioned optical water-quality detection apparatus could be disposed on the sensing base 400B. For example, the optical elements of the aforementioned optical water-quality detection apparatus 100 (for example, the biofilm-inhibited light source 110, the detection light source 120, the first sensor 130, the first light-splitting mirror 140, the first condensing lens 150 and the second condensing lens 160) and the optical elements (for example, the biofilm-inhibited light source 210, the first condensing lens 250 and the sensor 230) of the optical water-quality detection apparatus 200 could be disposed on the sensing base 400B. The sensing base 400B of the embodiment of the disclosure includes, for example, the optical water-quality detection apparatus 100 and 200; however, such exemplification is not meant to be for limiting.

As shown in FIG. 6, in the embodiment, the biofilm-inhibited light source 110 and the first condensing lens 150 are integrated into one piece. For example, the biofilm-inhibited light source 110 and the first condensing lens 150 directly connected with each other, or separated from each other (for example, that is, without physical connection). Similarly, the biofilm-inhibited light source 210 and the first condensing lens 250 are integrated into one piece. For example, the biofilm-inhibited light source 210 and the first condensing lens 250 directly connected with each other, or separated from each other (for example, that is, without physical connection). In an embodiment, the first condensing lens 150 could be a hemispherical lens having a first diameter, and the second condensing lens 160 could also be a hemispherical lens having a second diameter, and the first diameter is greater than or equal to the second diameter. The biofilm-inhibited light sources 110 and 210 could be disposed on a focus of the first condensing lens 150 and 250. Similarly, the detection light source 120 is disposed on a focus of the second condensing lens 160, so that the light emitted from the inhibition light source and the detection light source form parallel beams after traveling through these condensing lenses.

The first filter 435 is disposed between the first sensor 130 and the first light-splitting mirror 140. The first filter 435 and the first sensor 130 could contact directly, but could also be spaced apart from each other without contacting. The first filter 435 could allow a portion, having a specific wavelength, of the detection light L2 to travel through (but block the other portion of the detection light L2), thereby increasing the detection accuracy of the first sensor 130 for a specific composition. For example, when performing "SS detection", the first filter 435 could allow a portion, having the center wavelength of 850 nm, of the detection light L2 to travel through (but block the other portion, having the wavelength rather than the center wavelength of 850, of the detection light L2), thereby increasing the detection accuracy of the first sensor 130 for the suspended solids of the to-be-tested liquid in the liquid storage space R11. In another example, when performing "copper ion concentration detection", the first filter 435 could allow a portion, having the center wavelength of 450 nm, of the detection light L2 to travel through (but block the other portion, having the wavelength rather than the center wavelength of 450 nm, of the detection light L2), thereby increasing the detection accuracy of the first sensor 130 for the concentration of copper ions of the to-be-tested liquid in the liquid storage space R11.

In summary, the optical water-quality detection apparatus 400 provides two sets of independent detection optical paths, one set of the detection optical paths could perform a variety of different detections, for example, the SS detection and the copper ion concentration detection, and the other set of the detection optical paths could perform single detection, for example, COD detection.

In addition, the working sequence of the light sources in FIG. 6 could be the detection light source 120 (SS detection), the biofilm-inhibited light source 210 (COD detection) and the biofilm-inhibited light source 110 (biofilm inhibition) in sequence; however, such exemplification is not meant to be for limiting.

In addition, the sensing base 400B is detachably assembled with the detection chamber device 400A. As shown in FIG. 5, the holder 440 could detachably fixes the relative position of the detection chamber device 400A and the sensing base 400B, so that the sensing base 400B is detachably assembled with the detection chamber device 400A, so that the detection chamber device 400A could be quickly replaced with another detection chamber device 400A. In an embodiment, the holder 440 is, for example, an element having threaded.

Figure 7:
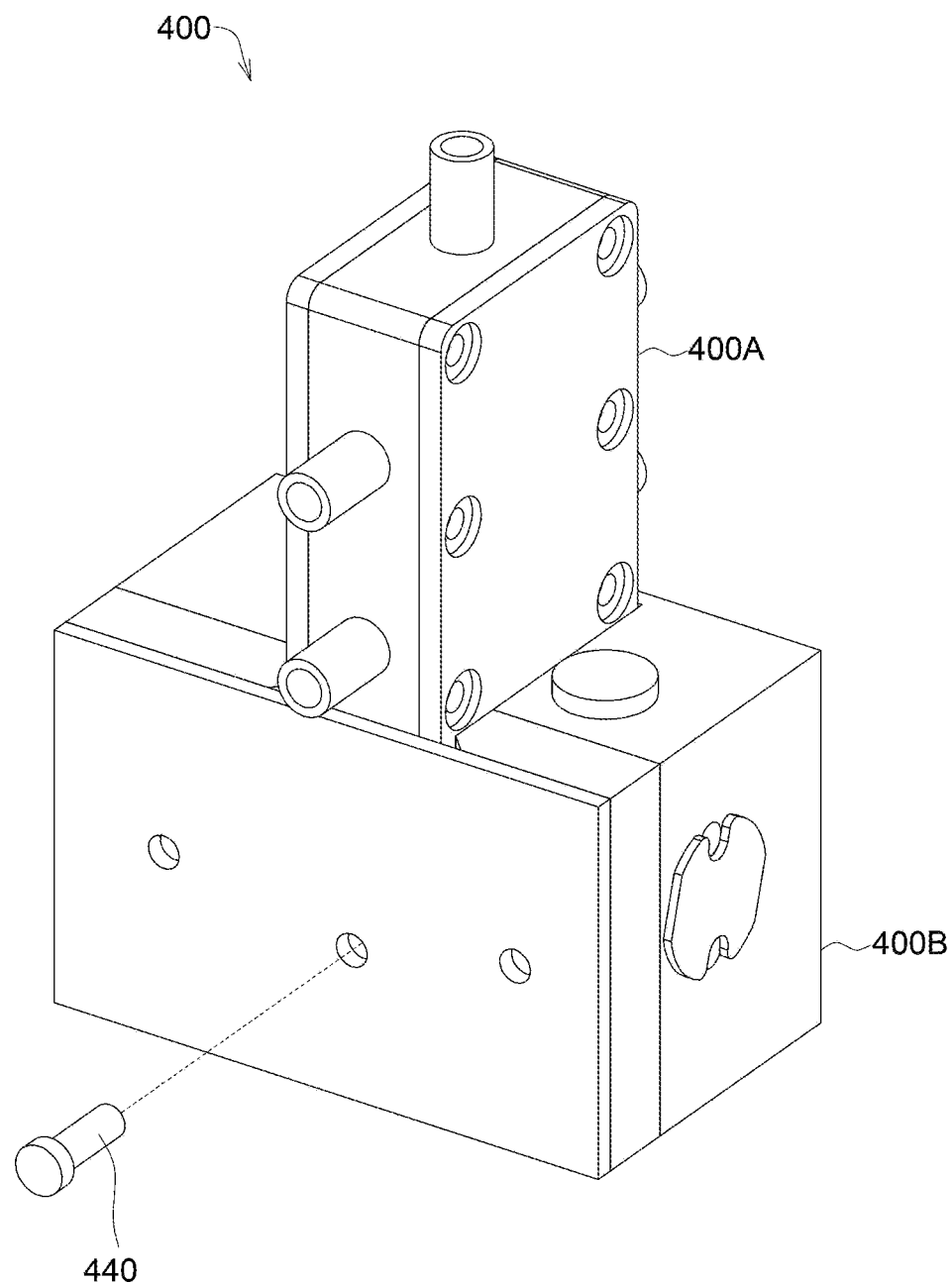
FIG. 7 shows a schematic diagram of the holder of FIG. 5 releasing the fixing relationship between the detection chamber device and the sensing base.
Figure 8:
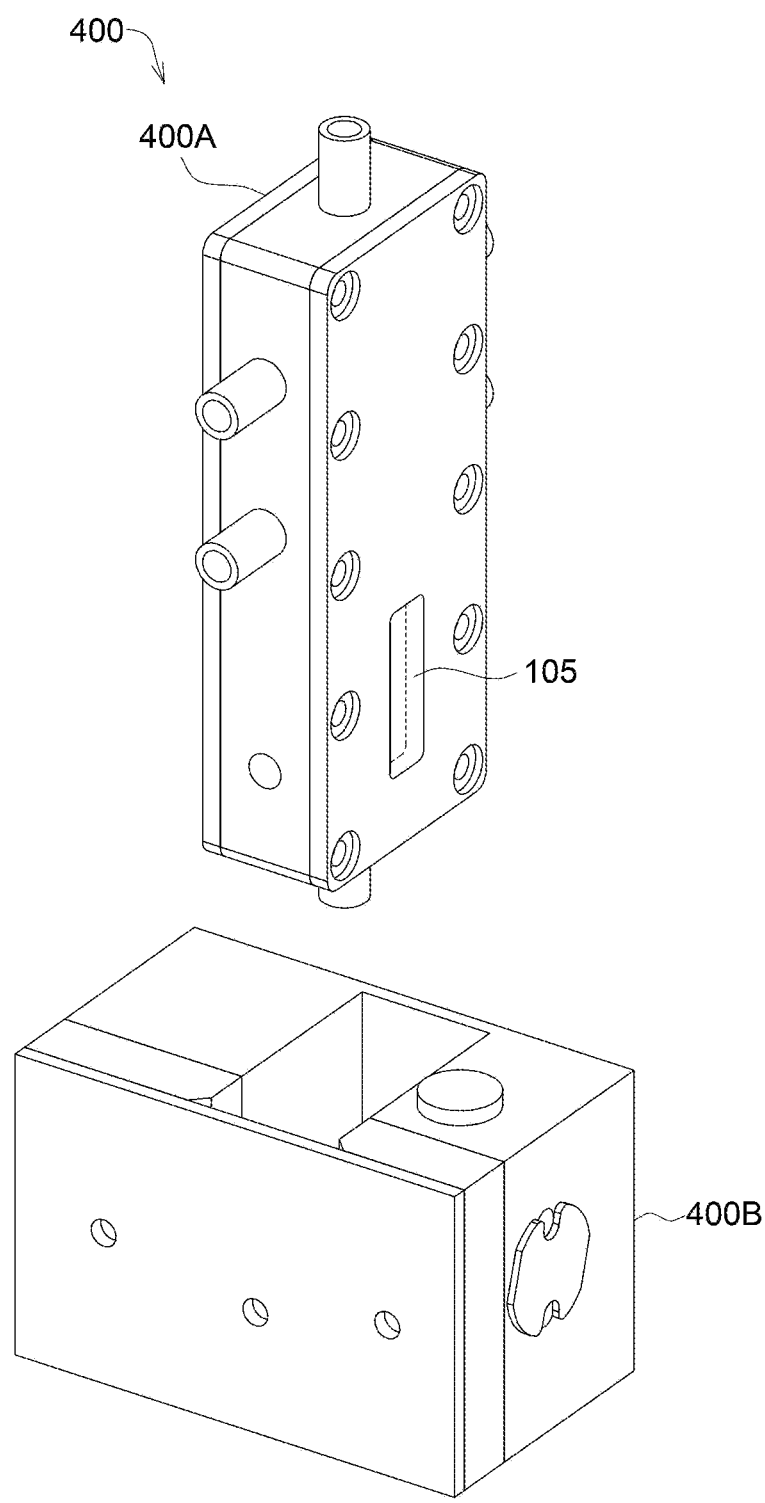
FIG. 8 shows a schematic diagram of the detection chamber device and the sensing base of FIG. 7.

Referring to FIGS. 7 to 8. FIG. 7 shows a schematic diagram of the holder 440 of FIG. 5 releasing the fixing relationship between the detection chamber device 400A and the sensing base 400B, and FIG. 8 shows a schematic diagram of the detection chamber device 400A and the sensing base 400B of FIG. 7. The detection chamber device 400A and the sensing base 400B are detachably connected. As shown in FIG. 7, when the holder 440 is released from the detection chamber device 400A and the sensing base 400B, the fixing relationship between the detection chamber device 400A and the sensing base 400B could be released. As shown in FIG. 8, when the fixed relationship between the detection chamber device 400A and the sensing base 400B is released, the detection chamber device 400A and the sensing base 400B could be separated. As a result, the disassembled detection chamber device 400A could be replaced with a new detection chamber device 400A (for example, the new detection chamber device 400A includes clean detection window 105) conveniently and quickly.

Figure 9:
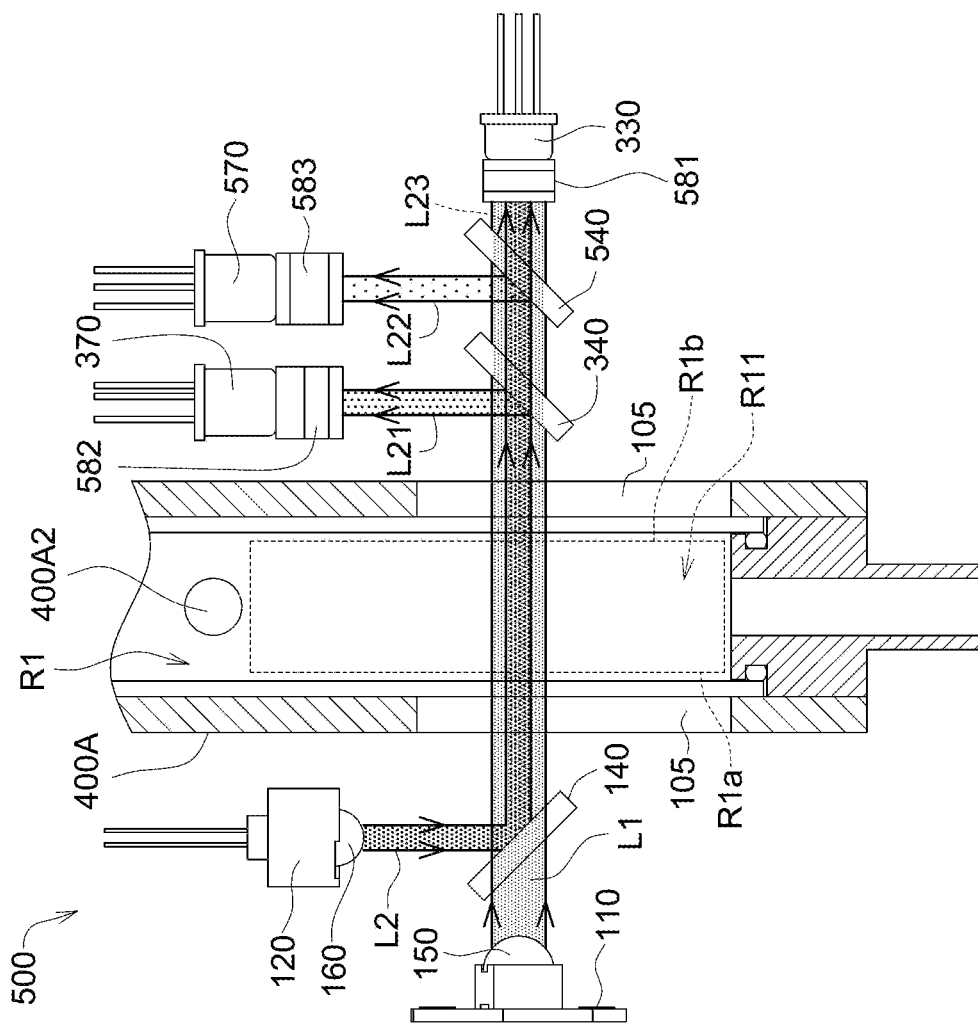
FIG. 9 shows a schematic diagram of a cross-sectional view of a detection chamber device of an optical water-quality detection apparatus according to another embodiment of the disclosure.

Referring to FIGS. 8 to 9, FIG. 9 shows a schematic diagram of a cross-sectional view of a detection chamber device 400A of an optical water-quality detection apparatus 500 according to another embodiment of the disclosure. The optical water-quality detection apparatus 500 includes the detection chamber device 400A, the sensing base 400B, at least one detection window 105, the biofilm-inhibited light source 110, the detection light source 120, the first sensor 330, the first light-splitting mirror 140, and the first condensing lens 150, the second condensing lens 160, the second light-splitting mirror 340, the second sensor 370, the third light-splitting mirror 540, the third sensor 570, the first filter 581, the second filter 582 and the third filter 583.

The optical elements of the aforementioned optical water-quality detection apparatus could be disposed on the sensing base 400B. For example, the optical elements of the aforementioned optical water-quality detection apparatus 300 (for example, the biofilm-inhibited light source 110, the detection light source 120, the first sensor 330, the first light-splitting mirror 140, the first condensing lens 150, the second condensing lens 160, the second light-splitting mirror 340 and the second sensor 370) are disposed on the sensing base 400B. In addition, the third light-splitting mirror 540, the third sensor 570, the first filter 581, the second filter 582 and the third filter 583 are also disposed on the sensing base 400B.

The second light-splitting mirror 340 is located outside the detection chamber R1 of the detection chamber device 400A and adjacent to the light-exit side R1$b$, and is configured to guide the first waveband light L21 of the detection light L2 to the second sensor 370. The third light-splitting mirror 540 is located outside the detection chamber R1 and adjacent to the light-exit side R1$b$, and is configured to guide the second waveband light L22 of the detection light L2 to the third sensor 570, wherein the first waveband light L21 has the wavelength different from that of the second waveband light L22. As a result, the second sensor 370 and the third sensor 570 could respectively react to different waveband light of the detection light L2 so as to detect several different types of characteristics of the to-be-tested liquid in the detection chamber R1.

In an embodiment, the second light-splitting mirror 340 could reflect light having the central wavelength of 850 nm, and accordingly the wavelength of the first waveband light L21 includes the central wavelength of 850 nm. The second sensor 370 could react to the first waveband light L21 and generate signal so as to detect the suspended solids of the test liquid in the detection chamber R1. The second filter 582 is disposed between the second sensor 370 and the second light-splitting mirror 340, and could allow the first waveband light L21, having the center wavelength of 850 nm, of the detection light L2 to travel through (but block the waveband light, having the wavelength rather than the center wavelength of 850 nm, of the detection light L2), thereby increasing the detection accuracy of the second sensor 370 for the suspended solids of the to-be-tested liquid in the liquid storage space R11.

The third light-splitting mirror 540 is, for example, a dichroic mirror, which allows the inhibition light L1 to travel through, but reflects the detection light L2, for example, the second waveband light L22 of the reflection detection light L2. In an embodiment, the third light-splitting mirror 540 could reflect light having the center wavelength of 450 nm, and thus the wavelength of the second waveband light L22 includes the center wavelength of 450 nm. The third sensor 570 could react to the second waveband light L22 and generate signal so as to detect the concentration of copper ions of the to-be-tested liquid in the detection chamber R1. The third filter 583 could be disposed between the third sensor 570 and the third light-splitting mirror 540, and could allow or only allow the second waveband light L22, having the center wavelength of 450 nm, of the detection light L2 to travel through (but block the waveband light, having the wavelength rather than the center wavelength of 450 nm, of the detection light L2), thereby increasing the detection accuracy of the third sensor 570 for the concentration of copper ions of the to-be-tested liquid in the liquid storage space R11.

As shown in FIG. 9, the second light-splitting mirror 340 is disposed between the detection chamber R1 and the third light-splitting mirror 540, and the detection light L2 travels through the second light-splitting mirror 340 and the third light-splitting mirror 540 in sequence. Furthermore, the first waveband light L21 of the detection light L2 is first reflected by the second light-splitting mirror 340 to the second sensor 370. Then, the other waveband light (having a shorter wavelength than the first waveband light L21) of the detection light L2 is incident into the third light-splitting mirror 540 after traveling through the second light-splitting mirror 340. In the other waveband light of the detection light L2, the second waveband light L22 whose wavelength is shorter than the first waveband light L21 is reflected by the third light-splitting mirror 540 to the third sensor 570. Then, the waveband, rather than the first waveband light L21 and the second waveband light L22, of the detection light L2 (hereinafter referred to as a third waveband light L23 whose wavelength is shorter than the first waveband light L21 and the second waveband light L22) continue to be incident into the first sensor 330.

The second light-splitting mirror 340 and the third light-splitting mirror 540 are disposed between the detection chamber R1 and the first sensor 330. As a result, after penetrating the detection chamber R1, the third waveband light L23 of the detection light L2 travels through the second light-splitting mirror 340 and the third light-splitting mirror 540 to the first sensor 330 in sequence.

In an embodiment, the center wavelength of the third wavelength band light L23 is, for example, 275 nm. The first sensor 330 is, for example, a GaN detector, which could react to the third waveband light L23 after the third waveband light L23 penetrates the detection chamber R1 and generate signal so as to detect the chemical oxygen demand of the to-be-tested liquid in the liquid storage space R11. The first filter 581 is disposed between the first sensor 330 and the third light-splitting mirror 540, and could allow the waveband light, having the center wavelength of 275 nm, of the detection light L2 to travel through but block the waveband light, having the wavelength rather than the center wavelength of 450 nm, of the detection light L2), thereby increasing the detection accuracy of the first sensor 130 for the chemical oxygen demand of the to-be-tested liquid in the liquid storage space R11. In addition, the range of the wavelength of the light that allows travel through the first filter 581, the second filter 582 and the third filter 583 could be changed according to the requirements of the detection item and the corresponding waveband of the used/selected light source.

In summary, the optical water-quality detection apparatus 500 provides one set of optical detection mechanisms which could simultaneously perform a variety of different detections, such as SS detection, COD detection, and copper ion concentration detection.

Figure 10:
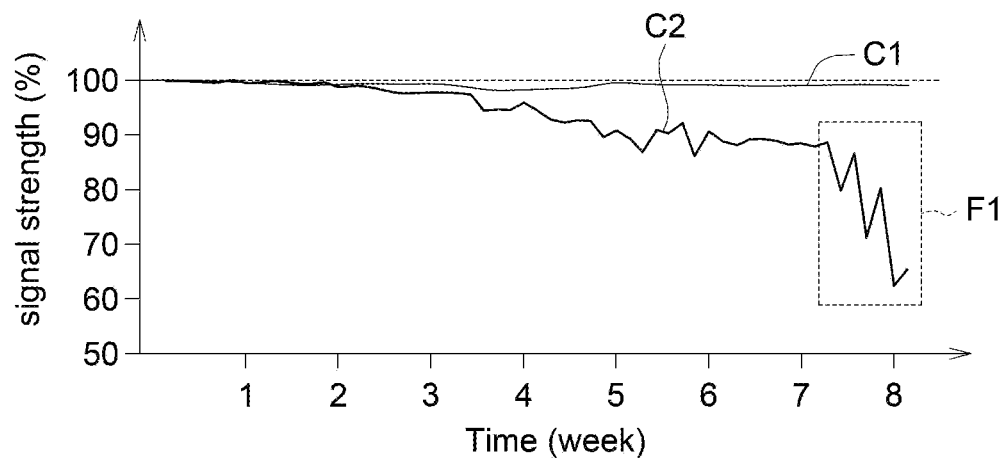
FIG. 10 shows a schematic diagram of an experimental result of the optical water-quality detection apparatus according to the embodiment of the disclosure.

Referring to FIG. 10, FIG. 10 shows a schematic diagram of an experimental result of the optical water-quality detection apparatus according to the embodiment of the disclosure. The axis of abscissa represents the experiment time, and the axis of ordinate represents the signal sensed by the sensor. The curve C1 represents the signal change of the optical water-quality detection apparatus of the embodiment of the disclosure within eight weeks of the experiment, and the curve C2 represents the signal change of the optical water-quality detection apparatus that does not use the biofilm-inhibited light source within eight weeks of the experiment. According to the experimental results, the signal (which is sensed by the sensor), after the optical water-quality detection apparatus (using the biofilm-inhibited light source of 12 mW) is actually tested for eight weeks (the curve C1), is reduced by only 1% to 2%. The signal, after the conventional optical water-quality detection apparatus that does not use the biofilm-inhibited light source is actually tested for eight weeks (the curve C2), is reduced by up to 36.5%, wherein the signal presents instability in the 7th to 8th weeks (as shown in dashed frame of FIG. 10), and it indicates that the sensed data is inaccurate. According to the experimental results, compared with the conventional optical water-quality detection apparatus that does not use the biofilm-inhibited light source, the optical water-quality detection apparatus of the disclosed embodiment could prolong the service life by 18 times.

In summary, the optical water-quality detection apparatus of the embodiment of the disclosure provides at least one detection optical path which could perform at least one characteristic/property detection of the to-be-tested liquid. In an embodiment, the optical water-quality detection apparatus includes the biofilm-inhibited light source and the detection light source, wherein the beam of the detection light emitted by the detection light source completely overlaps the beam of the inhibition light emitted by the biofilm-inhibited light source, accordingly it could simultaneously inhibit the biofilm for maintaining a proper accuracy of detection during detecting/inspecting the to-be-tested liquid.

It will be apparent to those skilled in the art that various modifications and variations could be made to the disclosed embodiments. It is intended that the specification and examples be considered as exemplary only, with a true scope of the disclosure being indicated by the following claims and their equivalents.

What is claimed is:

1. An optical water-quality detection apparatus, comprising:
   a detection chamber device comprising a detection chamber;
   a biofilm-inhibited light source disposed outside the detection chamber and configured to emit an inhibition light;

a detection light source disposed outside the detection chamber and configured to emit a detection light; and a first sensor configured to sense the detection light penetrating the detection chamber;

wherein a beam of the detection light and a beam of the inhibition light overlap each other when penetrating the detection chamber, wherein a spot area of a beam of the detection light is less than or equal to a spot area of a beam of the inhibition light.

2. The optical water-quality detection apparatus according to claim 1, further comprises:

a first light-splitting mirror disposed between the biofilm-inhibited light source or the detection light source and the detection chamber, wherein the first light-splitting mirror is configured to guide the inhibition light and the detection light into the detection chamber.

3. The optical water-quality detection apparatus according to claim 1, wherein the detection chamber comprises a light-incident side and a light-exit side, the inhibition light and the detection light enter the detection chamber through the light-incident side and leave the detection chamber through the light-exit side, the optical water-quality detection apparatus further comprises:

a second sensor disposed outside the detection chamber; and a second light-splitting mirror disposed outside the detection chamber and adjacent to the light-exit side, wherein the second light-splitting mirror is configured to guide a first waveband light of the detection light to the second sensor.

4. The optical water-quality detection apparatus according to claim 3, wherein the detection chamber device further comprises:

two detection windows being light-transmissive and respectively disposed on the light-incident side and the light-exit side of the detection chamber;

wherein the inhibition light and the detection light penetrate the detection chamber through the detection windows.

5. The optical water-quality detection apparatus according to claim 3, further comprises:

a third sensor disposed outside the detection chamber; and a third light-splitting mirror disposed outside the detection chamber and adjacent to the light-exit side, wherein the third light-splitting mirror is configured to guide a second waveband light of the detection light to the third sensor;

wherein a wavelength of the first waveband light is different from a wavelength of the second waveband light.

6. The optical water-quality detection apparatus according to claim 5, wherein the wavelength of the second waveband light is smaller than the wavelength of the first waveband light, and the second light-splitting mirror is disposed between the detection chamber and the third light-splitting mirror.

7. The optical water-quality detection apparatus according to claim 5, wherein the second light-splitting mirror and the third light-splitting mirror are disposed between the detection chamber and the first sensor.

8. The optical water-quality detection apparatus according to claim 5, further comprises:

a first filter disposed opposite to the first sensor and configured to allow a third waveband light of the detection light to travel through;

wherein a wavelength of the third waveband light, the wavelength of the second waveband light and the wavelength of the first waveband light are different.

9. The optical water-quality detection apparatus according to claim 8, further comprises:

a second filter disposed opposite to the second sensor and configured to allow the first waveband light of the detection light to travel through; and a third filter disposed opposite to the third sensor and configured to allow the second waveband light of the detection light to travel through.

10. The optical water-quality detection apparatus according to claim 1, wherein the detection chamber device further comprises:

two detection windows being light-transmissive and respectively disposed on two opposite sides of the detection chamber;

wherein the inhibition light and the detection light penetrate the detection chamber through the detection windows.

11. The optical water-quality detection apparatus according to claim 10, wherein the detection chamber device further comprises:

a liquid storage space disposed within the detection chamber;

a liquid inlet disposed in the detection chamber and communicating with the liquid storage space; and an overflow outlet communicating with the liquid storage space and having a central axis disposed between the two detection windows and the liquid inlet.

12. The optical water-quality detection apparatus according to claim 1, further comprises:

a sensing base detachably assembled with the detection chamber device; and a holder detachably fixing a relative position of the detection chamber device and the sensing base, wherein the biofilm-inhibited light source, the detection light source and the first sensor are disposed on the sensing base.

13. The optical water-quality detection apparatus according to claim 1, wherein the biofilm-inhibited light source is an ultraviolet light source.

14. The optical water-quality detection apparatus according to claim 1, wherein the detection light source is a halogen light source.

15. The optical water-quality detection apparatus according to claim 1, further comprises:

a first condensing lens connected with the biofilm-inhibited light source.

16. The optical water-quality detection apparatus according to claim 1, further comprises:

a second condensing lens connected with the detection light source.

* * * * *